United States Patent
Langhans et al.

(10) Patent No.: US 7,615,154 B2
(45) Date of Patent: Nov. 10, 2009

(54) LOOP REACTOR WITH CLOG-RESISTANT GAS DISTRIBUTION

(75) Inventors: Gerhard Langhans, Dresden (DE); Torsten Meyer, Klipphausen (DE)

(73) Assignee: Strabag Umweltanlagen GmbH, Dresden (DE)

( * ) Notice: Subject to any disclaimer, the term of this patent is extended or adjusted under 35 U.S.C. 154(b) by 217 days.

(21) Appl. No.: 11/497,516

(22) Filed: Aug. 2, 2006

(65) Prior Publication Data

US 2007/0125706 A1 Jun. 7, 2007

(30) Foreign Application Priority Data

Dec. 5, 2005 (DE) .......... 10 2005 057977

(51) Int. Cl.
*C02F 3/28* (2006.01)
*B01F 3/04* (2006.01)

(52) U.S. Cl. .......... 210/603; 210/220; 261/123
(58) Field of Classification Search .......... 210/603, 210/604, 220, 601; 261/123
See application file for complete search history.

(56) References Cited

U.S. PATENT DOCUMENTS

| | | | | |
|---|---|---|---|---|
| 2,519,533 A | * | 8/1950 | Arnett | 261/140.1 |
| 3,278,271 A | * | 10/1966 | Kono et al. | 422/225 |
| 3,561,735 A | * | 2/1971 | Smith | 261/34.1 |
| 4,341,641 A | * | 7/1982 | Novak | 588/320 |
| 5,650,070 A | * | 7/1997 | Pollock | 210/612 |
| 6,565,070 B2 | * | 5/2003 | Batterham et al. | 261/36.1 |

* cited by examiner

*Primary Examiner*—Fred Prince
(74) *Attorney, Agent, or Firm*—Millen, White, Zelano, Branigan, P.C.

(57) ABSTRACT

Special guide means 7 are located in the interior of a loop reactor for circulating the reactor contents. The guide means 7 has at least one central gas supply means 1 with gas distribution means 2 attached thereto for gas charging into the guide means 7. These loop reactors are used, e.g., as biogas reactors for treatment of biowastes or renewable raw materials. The gas distribution means 2 as gas guide elements are open to the bottom and are located above the gas exit openings 3 of the central gas supply means 1.

19 Claims, 4 Drawing Sheets

LOOP REACTOR WITH CLOG-RESISTANT GAS DISTRIBUTION

The invention relates to a loop reactor and a guide means located in the interior of the loop reactor for circulating the reactor contents, the guide means having at least one central gas supply means with gas distribution means attached thereto for gas charging into the guide means. The invention also relates to special gas guide elements as part of the gas distribution means.

Loop reactors are often used in process engineering. In this case, liquid or flowable media are treated in a reactor with circulation of the reactor contents. The reactor contents are routed from bottom to top through a central guide means, e.g., a vertical guide pipe into the interior of the reactor, and flow down again outside the guide pipe. For induction of the upward flow in the guide pipe, a gas is fed into the lower area of the guide pipe. The reactor contents are thus circulated in the form of a loop flow in the reactor.

Such loop reactors with internal loops are used as fully mixed, anaerobic suspension reactors in particular for biogas recovery from suspensions containing biodegradable substances, e.g., biowaste or renewable raw materials. This principle is described in, e.g., among others, CH 31 67 67 or DE 197 25 823 A1. In this case, immersed, biogas is blown into the bottom of the central guide pipe. The reduced density of the mixture in the guide pipe relative to the external liquid level yields a pressure difference in the liquid that induces a rising stream in the guide pipe. The injected biogas is to be distributed as uniformly as possible with bubbles as fine as possible over the guide pipe cross-section in order to ensure efficient mixture formation.

For small-diameter guide pipes, a gas-carrying ring line from which gas emerges inside on the guide pipe periphery via holes is often placed on the outside. For larger-diameter guide pipes, this principle is unfavorable since distribution over the cross-section is not achieved. Central feed nozzles on the bottom of the reactor under the guide pipe entry are likewise unfavorable for large fermentation reactors, since they do not significantly contribute to the driving pressure difference for gas feed nozzles located lower than roughly 14 m below the liquid surface due to the static pressure. The compressor rating for charging of the gas at the corresponding depth must, however, be applied.

For these reasons, for large reactors, lances immersed from the reactor roof are often inserted for supplying feed biogas preferably between 7 m and 12 m below the liquid level. In this case, according to the prior art, there are two alternatives with the advantages and disadvantages described below:

One alternative calls for the use of a central gas supply pipe with 3 to 7, preferably 5, gas distributor pipes of smaller diameter added to the lower end. The gas distributor pipes ensure gas emergence from the desired component circuit within the guide pipe and are thus designed to provide for an efficient mixture. This system has the advantage that a large-diameter supply pipe for gas can be used that can be made resistant to bending and vibration over a great immersion length. In practice, however, the laterally outgoing distributor pipes of small diameter are disadvantageous and can clog over time with incrustations and caking in highly concentrated suspensions, e.g., digested sludges. The gas emergence that thus takes place asymmetrically from unclogged, partially clogged and fully clogged pipes leads to disruptions of the sensitive hydraulic system.

In other alternatives, individual lances that are routed down are used separately on a component circuit. The latter offer a better cleaning possibility since they can be cleaned from the reactor roof over the entire length up to the gas exit. A problem however arises from inadequate mechanical stability due to the smaller individual pipe diameter relative to dynamic stresses and the shear forces imposed by floating parts in operation.

An object of this invention is to provide the gas supply and gas distribution means in loop reactors that have sufficient buckling resistance and flexural strength, and, with a low tendency to clogging so as to ensure efficient gas distribution.

Another object is to provide novel guide means.

Upon further study of the specification and appended claims, other objects and advantages of the invention will become apparent.

These objects are achieved according to the invention in that the gas distribution means are designed as gas guide elements having a top and a bottom, wherein the bottom is open and the top is located above the gas exit openings of the central gas supply means.

Existing designs assume routing the gas via pipes to the exit point. According to the invention, however, a design is proposed that has at least one central gas supply means that can comprise, for example, if a stable central middle pipe that extends under the liquid level up to the desired charging depth in the loop reactor. The gas distribution from this central gas supply means to the desired discharge component circuit in the guide means takes place, in contrast to the prior art, not via distributor pipes, but rather via gas guide elements that are open on the bottom and that cannot clog. Preferably, the gas guide elements are designed as sheets bent in a semicircle and open on the bottom. The central gas supply means is suitably designed as a vertical supply pipe that extends under the liquid level provided in the loop reactor. Preferably, the gas guide elements are attached to the outside of the central gas supply pipe. For example, they can be welded to the supply pipe when the supply pipe is made of metal and the gas guide elements are made as sheets bent in a semicircle.

Another possibility is the mounting of the radial guiding elements on a ring on the guide pipe. In this case the gas supply pipe should end on a ring mounted on the guide pipe with gas exit openings along the ring and inwardly directed radial guiding elements.

Depending on the application, three to seven, generally preferably five, gas guide elements at the height of the gas exit openings distributed over the pipe periphery are attached to the supply pipe. The gas exit openings in the supply pipe then enable gas passage under the gas guide elements. The latter are preferably tilted upward at an angle of between 5 degrees and 45 degrees against the horizontal, a tilt angle of between 10 degrees and 20 degrees being especially advantageous. The buoyancy forces cause the gas to flow under the preferably convexly arched top of the gas guide element along the outermost and innermost edges, where it separates as a chain of bubbles. The gas guide elements suitably have lateral guide surfaces that are drawn down in an elongated manner in the area around the gas discharge openings of the central gas supply means. As a result, this prevents the gas from emerging laterally under the gas guide elements in the area of turbulent gas passage. The gas thus reliably follows the guide contour of the gas guide elements. The top of the gas guide element is preferably imperforate, so as to avoid holes which can be clogged. However, it is also contemplated that advantages of this invention can be obtained even when the top is only substantially closed at the top, i.e. with not more than 50%, preferably not more than 90% of the gas bubbles leaving through holes in the top of the gas elements.

In general, after reactor circulation flow starts, the velocity of the rising liquid stream in the guide means, which is process-specific between 0.5 m per second and roughly 1.4 m per second, supports the gas flow under the gas guide elements and stabilizes the formation of a desired small-diameter bubble spectrum of between 10 mm and roughly 30 mm by the shear forces on the separation edges of the contour. At the same time, the liquid-gas flow along the gas guide elements causes a self-cleaning effect in which it washes caking and incrustations off the extension pieces.

The essential advantages of the device according to the invention comprise especially in the durability and clogging resistance of the gas charging system; this enables first of all economical, continuous operation especially in the treatment of high-solid suspensions. The use of a central gas supply means that can be designed as a stable central pipe in conjunction with gas guide elements that are attached thereto and that are open to the bottom overall yields a gas charging system with high resistance to buckling and bending. The central gas supply means can be easily cleaned by, e.g., inserting a pipe brush or a high-pressure cleaning head. The gas guide elements that are open to the bottom cannot clog, so that altogether the maintenance cost for the gas charging system can be minimized.

The invention is suitable for all conceivable loop reactors in which the reactor contents are recirculated via a guide means that is supplied with a gas for forming a propulsion jet. Especially advantageously, the invention can be used in biogas reactors for treatment of suspensions containing biodegradable substances in which, e.g., biowastes or renewable raw materials are fermented. Due to the high solids content of the suspension that is to be treated, an increased risk of clogging exists for the gas charging system especially in the treatment of renewable raw materials in biogas reactors. In such cases, the anti-clogging nature of the guide of this invention, offers very important advantages.

Embodiments of the invention are shown diagrammatically in the figures is to be explained in more detail below:

BRIEF DESCRIPTION OF THE DRAWINGS

FIG. 1 shows an extract from a loop reactor that can be used, for example, as a fully-mixed, anaerobic suspension reactor for treatment of biowastes or renewable raw materials. In the extract of the loop reactor, the guide means 7 designed as a guide pipe for forming the inner loop flow in the loop reactor is shown. In the guide pipe 7, there is a central supply pipe 1 for introducing gas into the guide pipe 7. The supply pipe 1 is inserted as a lance from overhead through the reactor roof 8. Underneath the intended liquid level in the loop reactor, the supply pipe 1 has gas exit opening 3 made as holes. In this area, gas guide elements 2 that are designed as sheets bent in a semicircular and open on the bottom are welded to the supply pipe 1. Gas distribution takes place from the central supply pipe 1 to the desired valved discharge component 6 in the guide pipe 7 via these gas distribution elements 2. In doing so, the gas exit openings 3 in the central supply pipe 1 enable gas passage under the gas guide elements 2 that are pointed upward at an angle of 10 to 20 degrees. The buoyancy forces cause the gas to flow under the convexly arched gas guide element as far as the outside edge where it separates as a chain of bubbles as shown in FIG. 1A. In doing so, the liquid-gas flow along the gas guide elements 2 causes a self-cleaning effect in which it washes caking and incrustations off the extension pieces. The central supply pipe 1 and the area of the gas discharge openings 3 under the gas guide elements 2 can be easily cleaned in operation. To do this, the central supply pipe 1 that is open to the bottom is extended 100 mm to 300 mm under the gas exit openings 3 as a guide section 4. The supply pipe 1 ends in the conventional manner above the reactor roof 8 with a blind flange 5 under which the gas supply 6 into the supply pipe 1 is bonded laterally. In the case of cleaning, this line can be blocked via a valve from the gas system. Then, via the removed blind flange input 5, a cleaning element, for example in the form of a pipe brush or a high-pressure cleaning head, can be inserted and lowered into the area of the gas exit openings 3. In this way, blockages can be reliably removed mechanically/hydraulically. During cleaning, no significant gas discharge from the central supply pipe 1 takes place, since in the lower area, it is, in effect, closed by the liquid level of the loop reactor. The guide section 4 open to the bottom on the central guide pipe 1 prevents the cleaning element from hanging up during operation at the height of the gas exit openings 3. Dislodged solids do not collect in the supply pipe 1, but rather sink through the lower opening into the reactor liquid. Gas does not emerge here in the operating state, since the static liquid column forces the injected gas to flow out of the higher gas exit openings 3 under the gas guide elements 2.

FIG. 2 relates to a detailed view of a radial gas guide element. In this case, it is a convexly bent sheet that is open to the bottom. FIG. 2A indicates how the radial guiding elements are fitted and after that folded along the symmetry axis (see attached FIG. 1A). The radial segment of the circle results from the folding process. The radius could be very small and has no functional meaning. In the area of the gas exit opening 3, the lateral guide surfaces 10 of the gas guide element are elongated and extend downwardly. This prevents the gas from discharging laterally under the gas guide element 2 in the area of turbulent gas passage through the gas exit opening 3. The gas thus reliably follows the guide contour of the gas element 2 as shown in FIG. 1A The top of the radial guiding element should be as close as possible above the gas exit openings. An increasing distance between the top of the radial guiding element and the gas exit opening results in a decreasing of the stability of the pressure difference between the inner sphere of the guide pipe (7, FIG. 1) and the outer sphere in the reactor. The shortest distance between the top of the radial guiding element and the gas exit opening is limited by the fillet weld between the radial guiding element and the gas exit opening. The gas flows through the outlet (3, FIGS. 1, 2) from gas supply pipe (1, FIG. 1) to the radial guiding elements (2, FIGS. 1, 2), where the gas stream is guided along the top of the radial guiding elements to the liquid. The bubbles exit the radial guiding elements on the lateral; edge (right side, FIG. 2). So the right side and the bottom of the radial guiding element in FIG. 2 are open.

FIG. 3 depicts an alternative embodiment where the bubbles emerge from a ring affixed to the walls of the reactor.

Figure 2:
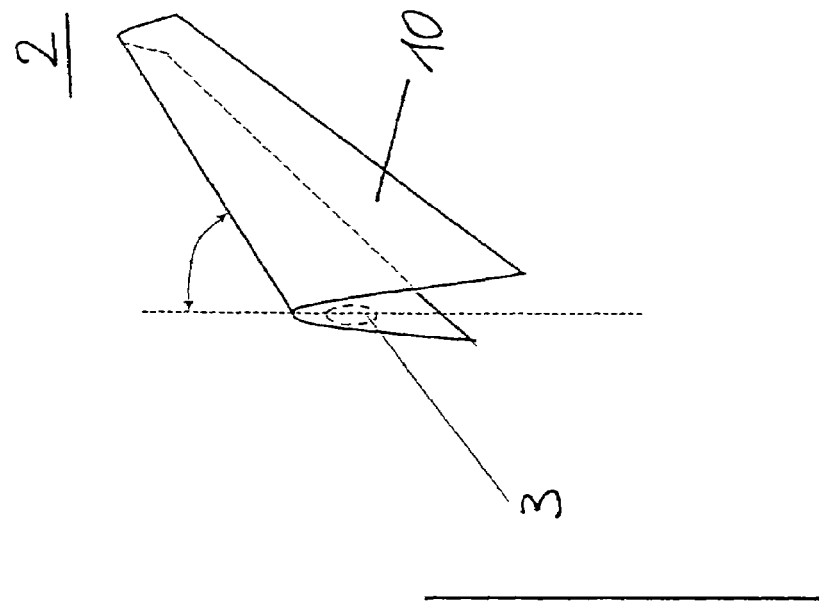
FIG. 2 shows a detailed view of a gas guide element.
Figure 1:
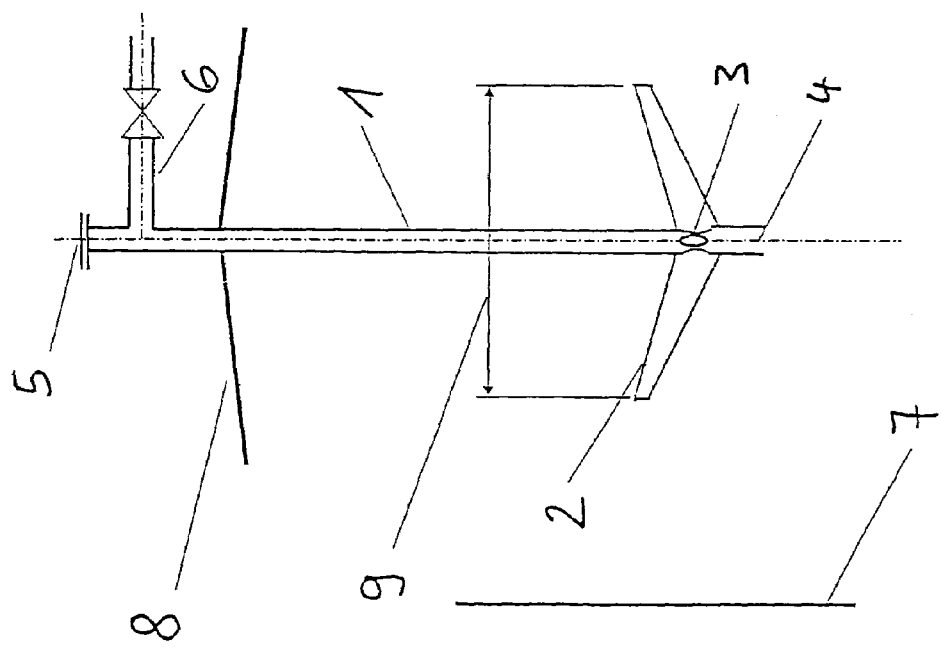
FIG. 1 shows a cross-section of a gas charging system for a loop reactor.
Figure 1A:
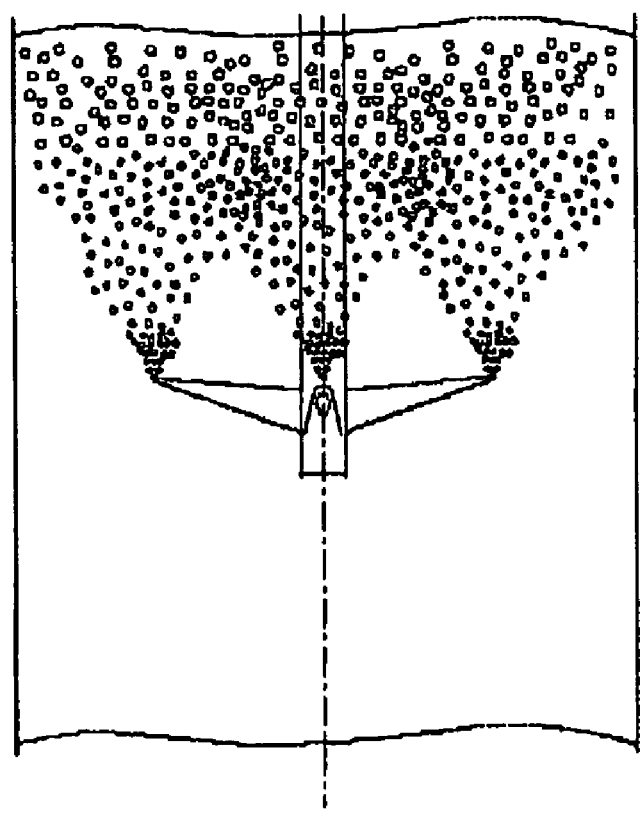
FIG. 1A shows gas bubbles energizing from the gas charging system.
Figure 2A:
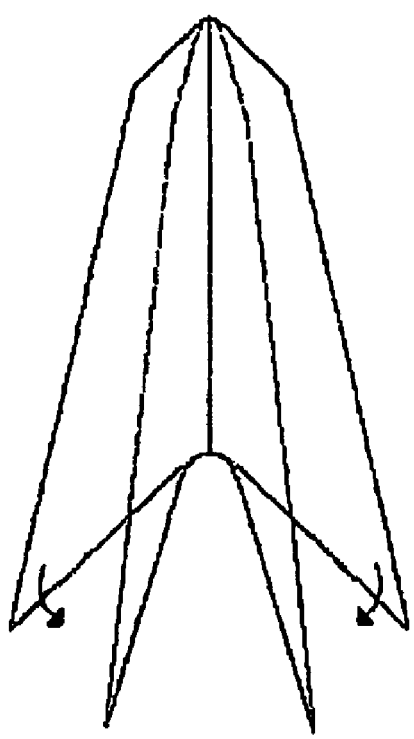
FIG. 2A shows how a gas guide element is bent.
Figure 3:
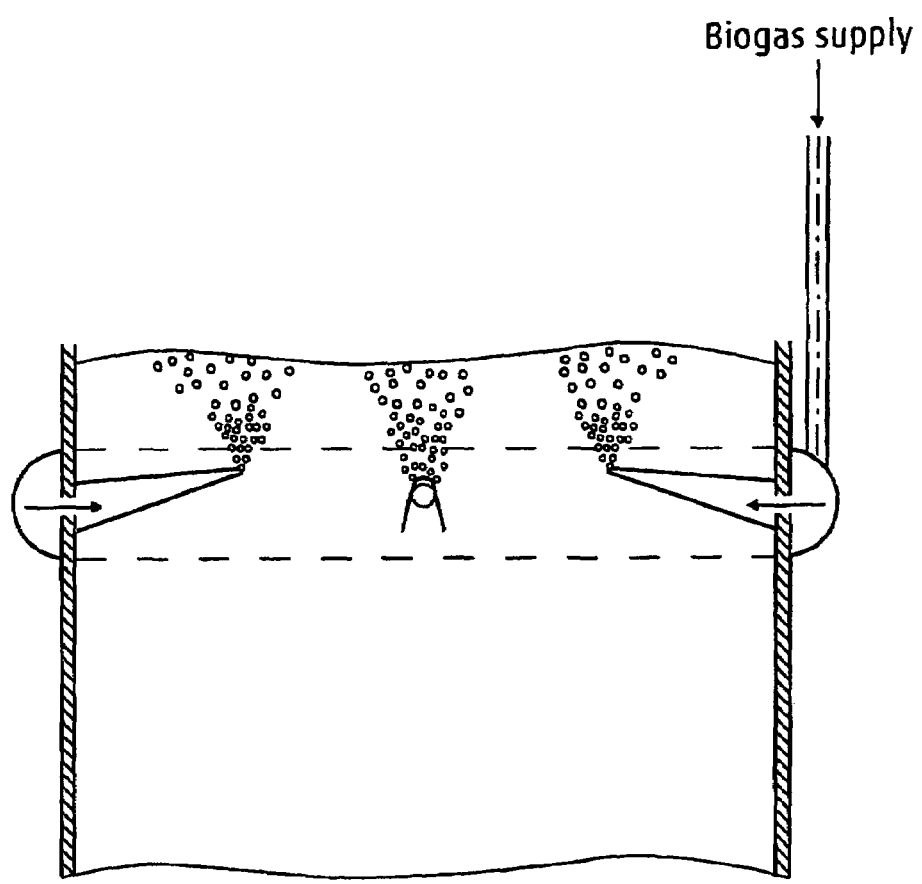
FIG. 3 shows an alternative construction.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

As a hypothetical example a reactor with a volume of 4000 $m^3$ filled with 3600 $m^3$ liquid could be used. The diameter of such a reactor is 16 m, the height is 22 m and the height of the liquid surface is 19 m. The central guide pipe has a diameter of 3 m. The central guide pipe reaches from 1.7 m above the lowest point of the bottom of the reactor to 1.5 m below the liquid surface. The gas supply pipe ends 11 m below the liquid surface (9.5 m below the upper end of the guide pipe). The radial length of the radial guiding elements is preferably between 30% and 70% of the radius of the guide pipe. From an external pump 400 m³/h are passed through the gas supply tube and therefore through the radial guiding elements. The outlet pressure of the pump compensates for the static pressure of a liquid column with a height of 11 m and the pressure losses along the whole gas tubing system including the safety equipment (approximately 100 mBar). The gas bubbles have a velocity of 1 m/s which leads to an average residence time of the bubbles in the guide pipe of approximately 10 s. This corresponds to a gas volume in the guide pipe of 0.8-1 m³ between the radial guiding elements and the upper end of the guide pipe. This gas volume decreases the static pressure of the 9.5 m liquid column by 120-150 mm. This pressure difference between the inner sphere of the guide pipe and the rest of the reactor results according to the Bernoulli equation in a theoretical liquid velocity in the guide pipe of 1.5-1.8 m/s. In practice the liquid velocity is in the range of 0.7-1.0 m/s due to hydraulic losses in the reactor. This leads to a volume of 20.000 m³ liquid (the fivefold volume of liquid in the reactor) which is pumped hourly through the guide pipe. An equal distribution of the bubbles keeps the pressure difference between the inner sphere of the guide pipe and the rest of the reactor stable.

In the specification and appended claims the term substantially imperforate means that not more than 50%, preferably not more than 10% of the gas bubbles leave through holes in the top of the gas element.

The preceding example can be repeated with similar success by substituting the generically or specifically described operating conditions of this invention for those used in the preceding example.

The entire disclosures of all applications, patents and publications cited herein, are incorporated by reference herein including but not limited to claimed German priority application DE 102005057977.9.

From the foregoing description, one skilled in the art can easily ascertain the essential characteristics of this invention, and, without departing from the spirit and scope thereof, can make various changes and modifications of the invention.

The invention claimed is:

1. In a method for anaerobic treatment of suspensions containing biodegradable substances, said method comprising providing a loop reactor and conducting anaerobic treatment in said loop reactor, said loop reactor comprising guide means located in the interior of the loop reactor for circulating reactor contents, the improvement wherein:
said guide means having at least one central gas supply means with gas distribution means attached thereto for charging gas into the guide means, said gas distribution means comprising gas guide elements in communication with gas exit openings in said at least one central gas supply means, each of said guide elements having a top section and a bottom section, the bottom sections being devoid of orifices and being substantially completely open to the reactor contents, and the top sections being located above the gas exit openings of said at least one central gas supply means.

2. A method of anaerobic treatment according to claim 1, wherein the gas guide elements are sheets bent in a semicircle and open on the bottom.

3. A method of anaerobic treatment according to claim 1, wherein said at least one central gas supply means comprises a vertical supply pipe of sufficient length to extend under a liquid level provided in the loop reactor.

4. A method of anaerobic treatment according to claim 3, wherein the gas guide elements are mounted externally on said vertical supply pipe.

5. A method of anaerobic treatment according to claim 4, wherein three to seven gas guide elements are attached to the vertical supply pipe and distributed over the periphery of the vertical supply pipe at the height of the gas exit openings the top sections of the gas guide elements being above but proximate to said gas exit openings.

6. A method of anaerobic treatment according to claim 1, wherein the gas guide elements are tilted upward at an angle of between 5 degrees and 45 degrees against the horizontal.

7. A method of anaerobic treatment according to claim 6, wherein the gas guide elements are tilted upward at an angle of between 10 degrees and 20 degrees against the horizontal.

8. A method of anaerobic treatment according to claim 1, wherein the gas guide elements (2) have elongated downwardly extending lateral guide surfaces.

9. A method of anaerobic treatment according to claim 1, wherein the gas guide elements extend radially outwardly from said at least one central gas supply means, said top sections of the gas guide elements being substantially imperforate.

10. A method of anaerobic treatment according to claim 9, said at least one central gas supply means being in communication with a bottom ring having openings along the ring and mounted on said guide means, said guide elements being attached to said openings and extending inwardly and upwardly towards said at least one central gas supply means.

11. A method of anaerobic treatment according to claim 10, wherein said top sections of the guide means are imperforate.

12. A method of anaerobic treatment according to claim 1, wherein the gas guide elements extend radially outwardly from said at least one central gas supply means, said top sections of the gas guide elements being imperforate.

13. A method according to claim 1, wherein said at least one central gas supply means being in communication with a bottom ring having openings along the ring and mounted on said guide means, and said guide elements being attached to said openings and extending inwardly and upwardly towards said at least one central gas supply means.

14. A loop reactor comprising:
a zone for anaerobic treatment, and
guide means, located in the interior of the anaerobic treatment zone, for circulating reactor contents,
said guide means having at least one central gas supply means with gas distribution means attached thereto for charging gas into the guide means,
said gas distribution means comprising gas guide elements in communication with gas exit openings in said at least one central gas supply means,
each of said guide elements having a top section and a bottom section, said bottom sections being devoid of orifices and being substantially completely open to the reactor contents, and
wherein three to seven of said gas guide elements are attached to said at least one central gas supply means and distributed over the periphery of said at least one central gas supply means at the height of the gas exit openings, the top sections of the gas guide elements being above but proximate to said gas exit openings.

15. A loop reactor comprising:

a zone for anaerobic treatment, and guide means, located in the interior of the anaerobic treatment zone, circulating reactor contents, said guide means having at least one central gas supply means with gas distribution means attached thereto for charging gas into said guide means, said gas distribution means comprising gas guide elements in communication with gas exit openings in said at least one central gas supply means, each of said guide elements having a top section and a bottom section, the bottom sections being devoid of orifices and being substantially completely open to the reactor contents and the top section being located above the gas exit openings of said at least one central gas supply means, and wherein the gas guide elements are tilted upward at an angle of between 5 degrees and 45 degrees against the horizontal.

16. A loop reactor according to claim 15, wherein said angle is between 10 to 20° against the horizontal.

17. A loop reactor comprising:

a zone for anaerobic treatment, and guide means, located in the interior of the anaerobic treatment zone, for circulating reactor contents, said guide means having at least one central gas supply means with gas distribution means attached thereto for charging gas into said guide means, said gas distribution means comprising gas guide elements in communication with gas exit openings in said at least one central gas supply means, each of said guide elements having a top section and a bottom section, the bottom sections being devoid of orifices and being substantially completely open to the reactor contents, and the top sections being located above the gas exit openings of said at least one central gas supply means, and wherein the gas guide elements extend radially outwardly from the central gas supply means, said top sections of the gas guide elements being imperforate.

18. A loop reactor according to claim 17, wherein the gas guide elements are tilted upward at an angle of between 10 degrees and 20 degrees against the horizontal.

19. A loop reactor comprising:

a zone for anaerobic treatment, and guide means, located in the interior of the anaerobic treatment zone, for circulating reactor contents, said guide means having at least one central gas supply means with gas distribution means attached thereto for charging gas into said guide means, said gas distribution means comprising gas guide elements in communication with gas exit openings in said at least one central gas supply means, each of said guide elements having a top section and a bottom section, the bottom sections being devoid of orifices and being substantially completely open to the reactor contents and the top sections being located above the gas exit openings of said at least one central gas supply means, said central gas supply means being in communication with a bottom ring having openings along the ring and mounted on the guide means, and said guide elements being attached to said openings and extending inwardly and upwardly towards said central supply means.

* * * * *

UNITED STATES PATENT AND TRADEMARK OFFICE
CERTIFICATE OF CORRECTION

| | | |
|---|---|---|
| PATENT NO. | : 7,615,154 B2 | Page 1 of 1 |
| APPLICATION NO. | : 11/497516 | |
| DATED | : November 10, 2009 | |
| INVENTOR(S) | : Langhans et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 317 days.

Signed and Sealed this

Nineteenth Day of October, 2010

David J. Kappos
*Director of the United States Patent and Trademark Office*